US009908926B2

(12) United States Patent
Van Horn et al.

(10) Patent No.: US 9,908,926 B2
(45) Date of Patent: Mar. 6, 2018

(54) PROTEIN-BASED MOLECULAR TEMPERATURE SWITCH

(71) Applicant: ARIZONA BOARD OF REGENTS ON BEHALF OF ARIZONA STATE UNIVERSITY, Scottsdale, AZ (US)

(72) Inventors: Wade Van Horn, Mesa, AZ (US); Nicholas Sisco, Chandler, AZ (US); Parthasarathi Rath, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 15/118,358

(22) PCT Filed: Feb. 11, 2015

(86) PCT No.: PCT/US2015/015464
§ 371 (c)(1),
(2) Date: Aug. 11, 2016

(87) PCT Pub. No.: WO2015/123331
PCT Pub. Date: Aug. 20, 2015

(65) Prior Publication Data
US 2017/0174739 A1 Jun. 22, 2017

Related U.S. Application Data

(60) Provisional application No. 61/940,669, filed on Feb. 17, 2014.

(51) Int. Cl.
C07K 14/705 (2006.01)
G01N 24/08 (2006.01)

(52) U.S. Cl.
CPC ......... *C07K 14/705* (2013.01); *G01N 24/088* (2013.01); *C07K 2319/00* (2013.01)

(58) Field of Classification Search
None
See application file for complete search history.

(56) References Cited

U.S. PATENT DOCUMENTS

2007/0105155 A1  5/2007  Qin
2007/0196816 A1  8/2007  Schwartz et al.
2007/0295907 A1  12/2007  Brott et al.

OTHER PUBLICATIONS

Butterwick et al., Solution structure and phospholipid interactions of the isolated voltage-sensor domain from KvAP, Nov. 5, 2010J. Mol. Biol. 403(4): 591-606.*
Jiang et al., X-ray structure of a voltage-dependent K1 channel, May 1, 2003, Nature 423:33-41.*
Kalia et al., Exploring structure-function relationships between TRP and Kv channels, Mar. 22, 2013, Scientific Reports 3:1523 | DOI: 10.1038/srep01523, pp. 1-9.*
Minke et al., Insights on TRP Channels from in Vivo Studies in *Drosophila.*, Annual Review of Physiology, 2006, 68:649-84.
Cosens et al., Abnormal Electroretinogram from a *Drosophila* Mutant., Nature, Oct. 1969, 224(5216):285-7.
Montell et al., Molecular characterization of the *Drosophila* trp locus: A putative integral membrane protein required for phototransduction., Neuron, Apr. 1989, 2(4):1313-23.
Wong et al., Proper function of the *Drosophila* trp gene product during pupal development is important for normal visual transduction in the adult., Jul. 1989, Neuron, 3(1):81-94.
Minke et al., Inositol lipid pathway in fly photoreceptors: excitation, calcium mobilization and retinal degeneration., Progress in Retinal Research, 1991, 11:99-124.
Hardie et al., The trp gene is essential for a light-activated Ca2+ channel in *Drosophila* photoreceptors., Neuron, Apr. 1992, 8(4):643-51.
Wes et al., TRPC1, a human homolog of a *Drosophila* store-operated channel., PNAS USA, Oct. 1995, 92:9652-56.
Zhu et al., Molecular cloning of a widely expressed human homologue for the *Drosophila* trp gene., FEBS Letters, Oct. 1995, 373(3):193-8.
Proudfoot et al., Analgesia Mediated by the TRPM8 Cold Receptor in Chronic Neuropathic Pain., Current Biology, Aug. 2006, 16(16)1591-1605.
Gottschalk et al., New Concepts in Acute Pain Therapy: Preemptive Analgesia., American Family Physician, May 2001, 63(10):1979-84.
Li et al., Menthol induces cell death via the TRPM8 channel in the human bladder cancer cell line T24., Oncology, Feb. 2010, 77(6):335-41.
Bandell et al., High-throughput random mutagenesis screen reveals TRPM8 residues specifically required for activation by menthol., Nature Neuroscience, Apr. 2006, 9(4):493-500.
Malkia et al., Differential role of the menthol-binding residue Y745 in the antagonism of thermally gated TRPM8 channels., Molecular Pain, Nov. 2009, 5:62(13 pages).
Voets et al., The principle of temperature-dependent gating in cold- and heat-sensitive TRP channels., Nature, Aug. 2004, 430:748-754.
Zakharian et al., Gating of Transient Receptor Potential Melastatin 8 (TRPM8) Channels Activated by Cold and Chemical Agonists in Planar Lipid Bilayers., Journal of Neuroscience, Sep. 2010, 30(37):12526-34.
Tajino et al., Cooling-Sensitive TRPM8 Is Thermostat of Skin Temperature against Cooling., PLoS One, Mar. 2011, 6(3):e17504(6 pages).
Pertusa et al., N-Glycosylation of the TRPM8 Ion Channels Modulates Temperature Sensitivity of Cold Thermoreceptor Neurons., Journal of Biological Chemistry, May 2012, 287(22):18218-29.

(Continued)

*Primary Examiner* — John D Ulm
(74) *Attorney, Agent, or Firm* — Jiarong L. Lamiquiz; Quarles & Brady LLP

(57) ABSTRACT

A region of the TRPM8 protein that functions as a temperature switch (FIG. 1) has been identified, and can be expressed, purified and applied in combination with other proteins. The function of the switch is maintained even when the region or domain is isolated from the entire protein. As the protein domain is a temperature switch, it can be used to control other proteins and signaling pathways in vitro and in vivo; and 2) TRPM8 is a therapeutic target that is being pursued primarily for intervention in pain (neuropathic and inflammatory) and cancer.

16 Claims, 14 Drawing Sheets

(56) References Cited

OTHER PUBLICATIONS

Pedretti et al., Comparative modeing of the quaternary structure for the human TRPM8 channel and analysis of its binding features., Biochemica et Biophysica Acta (BBA)—Biomembranes, May 2009, 1788:973-82.
Phelps et al., The Role of the N Terminus and Transmembrane Domain of TRPM8 in Channel Localization and Tetramerization., Journal of Biological Chemistry, Dec. 2007, 282(50):36474-80.
Van Horn et al., Protein—based Molecular Temperature Switch., AzTE Disclosure, 2014, 1 page.
Van Horn et al., "Biophysical Characterization of the TRPM8 Voltage-Sensing Domain," Biophysical Journal, vol. 106, Issue 2, p. 756a (Jan. 2014).

* cited by examiner

PROTEIN-BASED MOLECULAR TEMPERATURE SWITCH

CROSS-REFERENCE TO RELATED APPLICATIONS

This application is a 371 application of PCT/US2015/015464 filed Feb. 11, 2015, which is based on, claims a priority benefit from, and incorporates herein by reference, U.S. Provisional Patent Application No. 61/940,669, filed Feb. 17, 2014 and entitled "A Protein-Based Molecular Temperature Switch."

This invention was made with government support under R01 GM112077 awarded by the National Institutes of Health. The government has certain rights in the invention.

BACKGROUND OF THE INVENTION

TRPM8 is a protein that was initially identified as an oncogene. It is a membrane protein ion channel that primarily functions as the main cold temperature sensor in higher organisms. TRPM8 is modulated or regulated directly by a number of different types of stimuli in addition to temperature; including, small molecules (both natural and synthetic), voltage, lipids, and other proteins. Notwithstanding the role in thermosenstaion, there has been tremendous interest in the protein because early on it was shown to be involved in a number of types of cancer. More recently TRPM8 has been shown to be an excellent target for neuropathic and inflammatory pain as evidenced by a number of pharmaceutical companies pursuing this target.

Similarly, it has been shown to be involved in thermogenesis which has been shown to regulate important physiological processes. Among these is obesity, which has direct effects on things like diabetes and heart disease. Researchers showed that by activating TRPM8, they could make obese mice models loose significant weight, suggesting that in addition to pain and cancer, new rounds of screening for obesity and related therapeutics will likely be developed in the near future. Most recently, it was shown that TRPM8 is important for withdrawal syndrome from opiates hinting at additional opportunities for drug development.

SUMMARY OF THE INVENTION

The embodiments described herein relate to regulation of protein domains, specifically the controlled regulation of membrane proteins by thermosensitive voltage-sensitive domains.

In one aspect, certain embodiments relate to a method of regulating protein conformation including associating a protein and a voltage sensitive protein domain to form a protein switch and regulating a conformation of the protein switch by changing a temperature of the protein switch such that the protein switch conformation after changing the temperature varies from the protein switch conformation before the temperature change.

In another aspect, certain embodiments relate to a kit A kit for protein conformation regulation including an isolated voltage sensitive protein domain, the voltage sensitive domain configured to regulate a protein conformation during a temperature change from an initial temperature to a changed temperature.

We have identified a region of the TRPM8 protein that functions as a temperature switch. This function is maintained even when the region or domain is isolated from the entire protein. We have optimized a framework to express and purify this domain and incorporate it into multiple environments and the functionality is maintained suggesting that development of this domain may have practical use in biotechnology.

We envision two main roles for this domain: 1) As the protein domain is a temperature switch it could be used to control other proteins and signaling pathways in vitro and in vivo, especially as the field of synthetic biology progresses; and 2) TRPM8 is a therapeutic target that is being pursued primarily for intervention in pain (neuropathic and inflammatory) and cancer (mostly prostate) by various companies.

Many of the therapeutics under development target the temperature switch domain of the protein attempting to render it exclusively in the "on" or "off" position. With the knowledge of the domain we can lock it into either the "on" or "off" conformation or a mixture of states which could serve as a conformation dependent target for drug screening applications that would allow for development of conformation specific targeting for therapeutic design.

These and other aspects of the invention will be apparent upon reference to the following detailed description and figures. To that end, any patent and other documents cited herein are hereby incorporated by reference in their entirety.

DETAILED DESCRIPTION OF THE INVENTION

Figure 1:
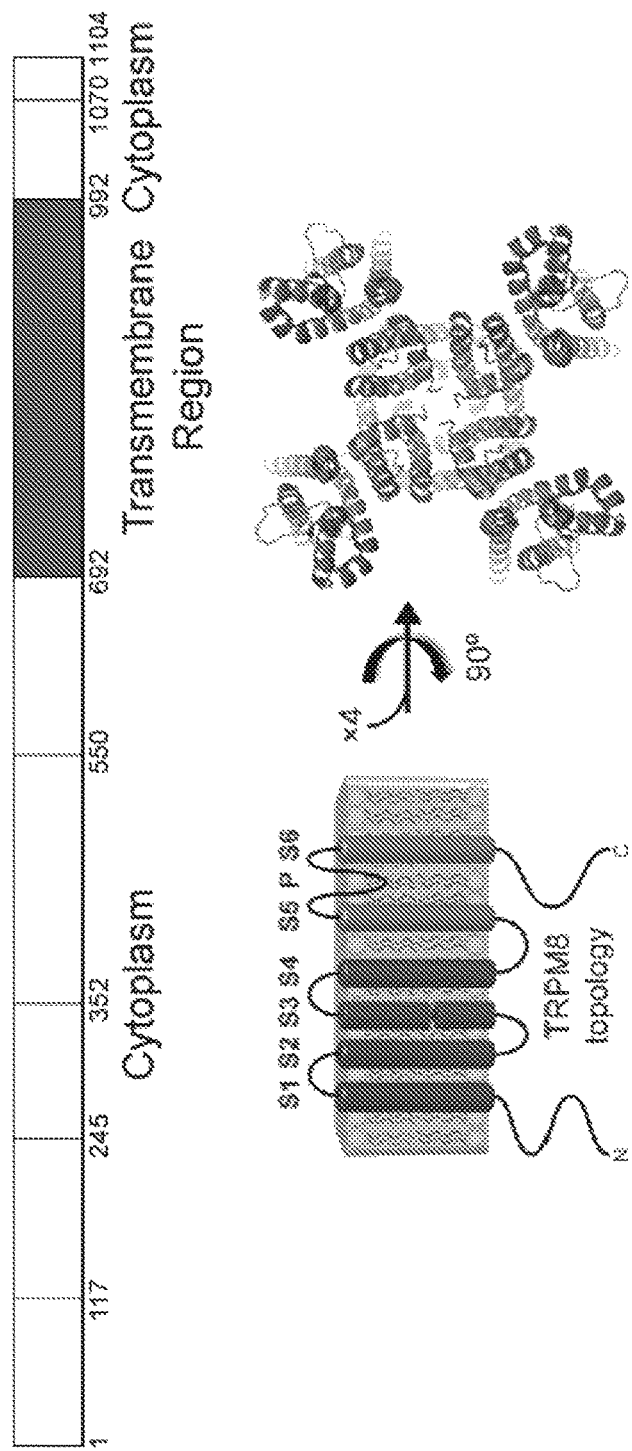
FIG. 1 illustrates schematic and crystallographic views of the TRPM8 protein domain morphology.

Embodiments described herein relate to gene products, specifically gene products that function as thermosensors.

One of the fundamental ways that TRPM8 is regulated is via temperature. A fraction of the human TRPM8 gene product that functions as the switch that controls TRPM8 thermosensation has been isolated. After evaluation of hundreds of conditions, the voltage-sensor domain (VSD) protein domain has been identified as responsible for thermosensation. The isolated VSD has practical applicability as a molecular switch and as an element in drug screening against specific conformations of TRPM8.

A protein domain is a conserved part of a given protein sequence and structure that can evolve, function, and exist independently of the rest of the protein chain. Each domain forms a compact three-dimensional structure and often can be independently stable and folded. Many proteins consist of several structural domains. One domain may appear in a variety of different proteins. Molecular evolution uses domains as building blocks and these may be recombined in different arrangements to create proteins with different functions. Domains vary in length from between about 25 amino acids up to 500 amino acids in length. The shortest domains such as zinc fingers are stabilized by metal ions or disulfide bridges. Domains often form functional units, such as the calcium-binding EF hand domain of calmodulin. Because they are independently stable, domains can be "swapped" by genetic engineering between one protein and another to make chimeric proteins.

Voltage-gated ion channels are a class of transmembrane ion channels that are activated by changes in electrical membrane potential near the channel; these types of ion channels are especially critical in neurons, but are common in many types of cells.

Voltage-gated ion channels have a crucial role in excitable neuronal and muscle tissues, allowing a rapid and co-ordinated depolarization in response to triggering voltage change. Found along the axon and at the synapse, voltage-gated ion channels directionally propagate electrical signals.

Voltage-gated ion channels generally are composed of several subunits arranged in such a way that there is a central pore through which ions can travel down their electrochemical gradients. The channels tend to be ion-specific, although similarly sized and charged ions may sometimes travel through them.

From crystallographic structural studies of a voltage-gated ion channel, assuming that the structure remains intact in the corresponding plasma membrane, it is possible to surmise that when a potential difference is introduced over the membrane, the associated electromagnetic field induces a conformational change in the ion channel. The conformational change distorts the shape of the channel proteins sufficiently such that the cavity, or channel, opens to admit ion influx or efflux to occur across the membrane, down its electrochemical gradient. This subsequently generates an electrical current sufficient to depolarise the cell membrane.

Voltage-gated sodium channels and calcium channels are made up of a single polypeptide with four homologous domains. Each domain contains 6 membrane spanning alpha helices. One of these helices, S4, is the voltage sensing helix. It has many positive charges such that a high positive charge outside the cell repels the helix, keeping the channel in its closed state. Depolarization of the cell interior causes the helix to move, inducing a conformational change such that ions may flow through the channel (the open state). Potassium channels function in a similar way, with the exception that they are composed of four separate polypeptide chains, each comprising one domain.

The voltage-sensitive protein domain of these channels (the "voltage sensor") generally contains a region composed of S3b and S4 helices, known as the "paddle" due to its shape, which appears to be a conserved sequence, interchangeable across a wide variety of cells and species. A similar voltage sensor paddle has also been found in a family of voltage sensitive phosphatases in various species. Genetic engineering of the paddle region from a species of volcano-dwelling archaebacteria into rat brain potassium channels results in a fully functional ion channel, as long as the whole intact paddle is replaced. This "modularity" allows use of simple and inexpensive model systems to study the function of this region, its role in disease, and pharmaceutical control of its behavior rather than being limited to poorly characterized, expensive, and/or difficult to study preparations.

Transient Receptor Potential (TRP) Channels were first discovered in Drosophila and named after their role in phototransduction. They are a very diverse superfamily including ion selectivities, modes of activation, and physiological functions. There are twenty seven TRP channels in humans expressed predominantly in the nervous system. These channels function in sensory physiology and are responsible for human vision, taste, smell, hearing, mechanosensation, and thermosensation.

Figure 2:
FIG. 2 illustrates the amino acids that comprise the transmembrane TRPM8 protein domain (SEQ ID NO: 1) that provide the thermosensitivity of the protein domain.
Figure 3:
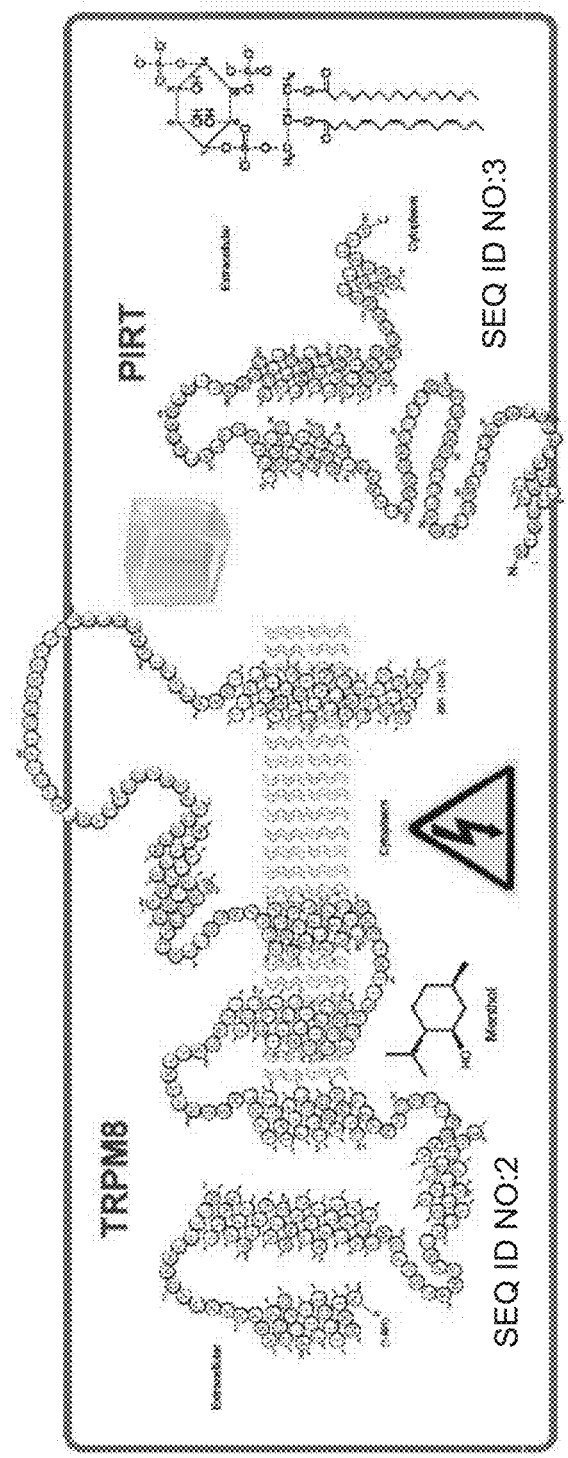
FIG. 3 illustrates the regulation of the ion channel (SEQ ID NO: 2) via cold temperature change to an open channel within the protein membrane in the presence of PIRT (SEQ ID NO: 3)

FIGS. 1-3 illustrate various aspects of the TRPM8 protein domain. FIG. 1 illustrates schematic and crystallographic views of the TRPM8 protein domain morphology. FIG. 2 illustrates the amino acids that comprise the transmembrane TRPM8 protein domain that provide the thermosensitivity of the protein domain. TRPM8 is identified as a cold and menthol activated ion channel that is up-regulated in various cancers. The TRPM8 is a nonselective cation channel that is found primarily in afferent neurons of dorsal root ganglia and functions as the primary cold sensor in humans. TRPM8 may be used as a therapeutic target in cancer treatments. For example, siRNAs targeting TRPM8 protein domains elicit apoptosis in prostate and pancreatic cancer cell lines suggesting that it has promise as a target for cancer therapy. In another embodiment, menthol targets the TRPM8 protein domain and induces cell death in human bladder cancer cell lines.

Figure 4:
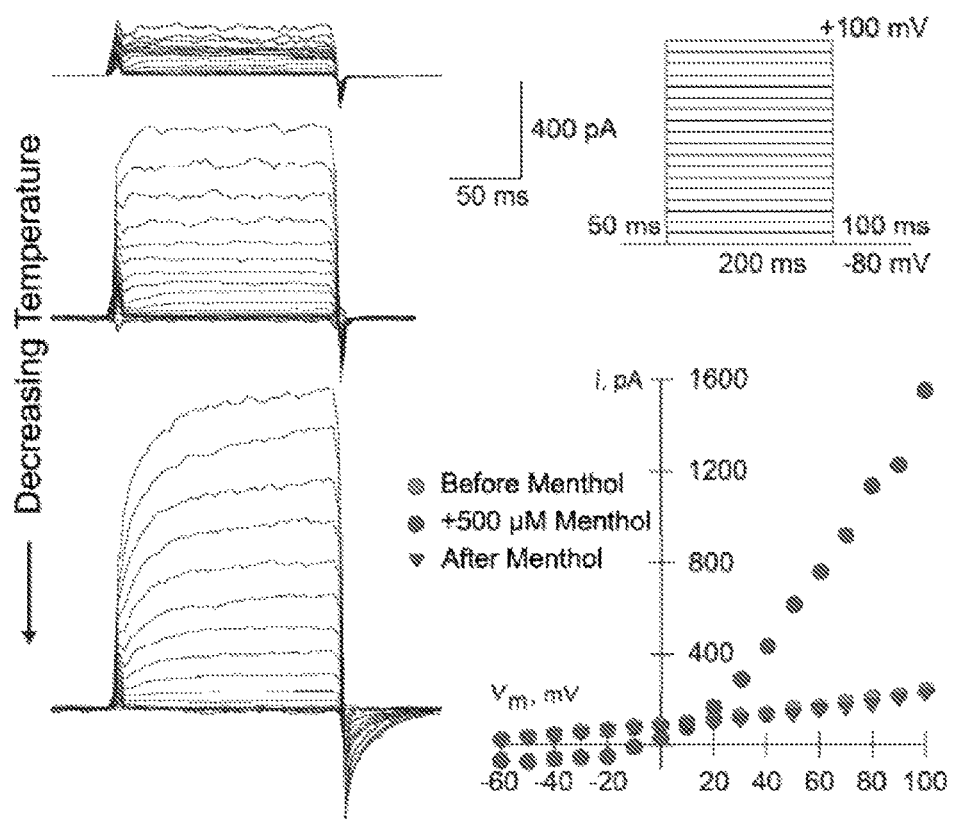
FIG. 4 is a depiction of the data analysis of the opening of the TRPM8 protein domain ion channel upon temperature cooling.
Figure 5:
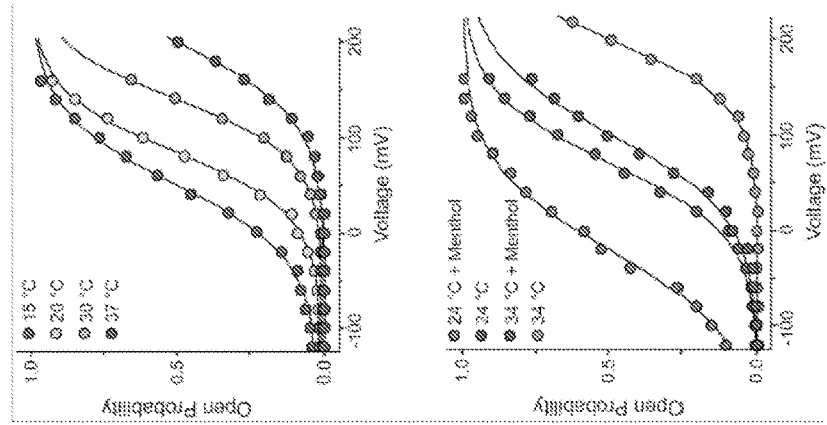
FIG. 5 shows an NMR spectra obtained during menthol titration of a TRPM8-VSD.
Figure 6:
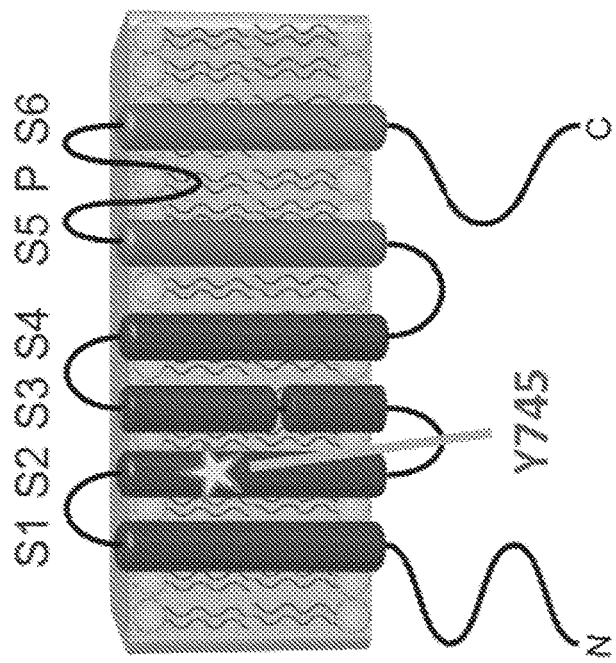
FIG. 6 illustrates the binding of menthol to the Tyrosine 745 residue in the S2 helix of the TRPM8-VSD.
Figure 7:
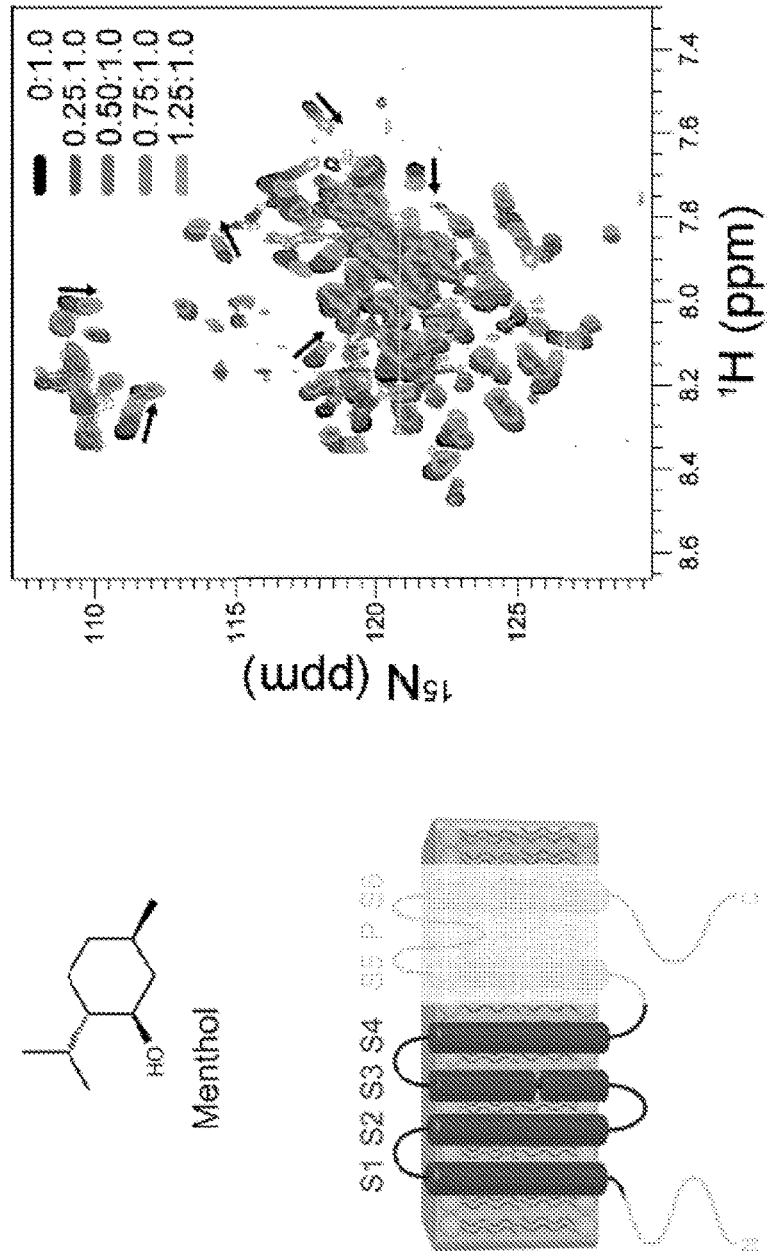
FIG. 7 illustrates TROSY-HSQC NMR spectra data collected during titration of TRPM8-VSD with menthol.

FIG. 3 illustrates the regulation of the ion channel via cold temperature change to an open channel within the protein membrane. The TRPM8 protein domain is weakly voltage-dependant and polymodal in that it can be activated with more than one agonist. For example, and as shown in FIGS. 4 and 5, cold activates TRPM8 by shifting the voltage dependence of activation. In another embodiment, menthol activates the TRPM8 protein domain by shifting the activation curve as shown in FIG. 5. The menthol molecule binds the TPM8 voltage sensing domain at the Tyrosine 745 in the S2 helix (shown in FIG. 6) to activate the domain. Titration of TRPM8-VSD with menthol was conducted at ambient temperature using ratios of about 0.25:1.0, about 0.50:2.0, about 0.75:1.0, and about 1.25:1.0. As shown in FIG. 7, titration of TRPM8-VSD with menthol results in a conformational change of the protein domain demonstrated by the shift of the protons shown in the TROSY-HSQC NMR spectra.

Figure 8:
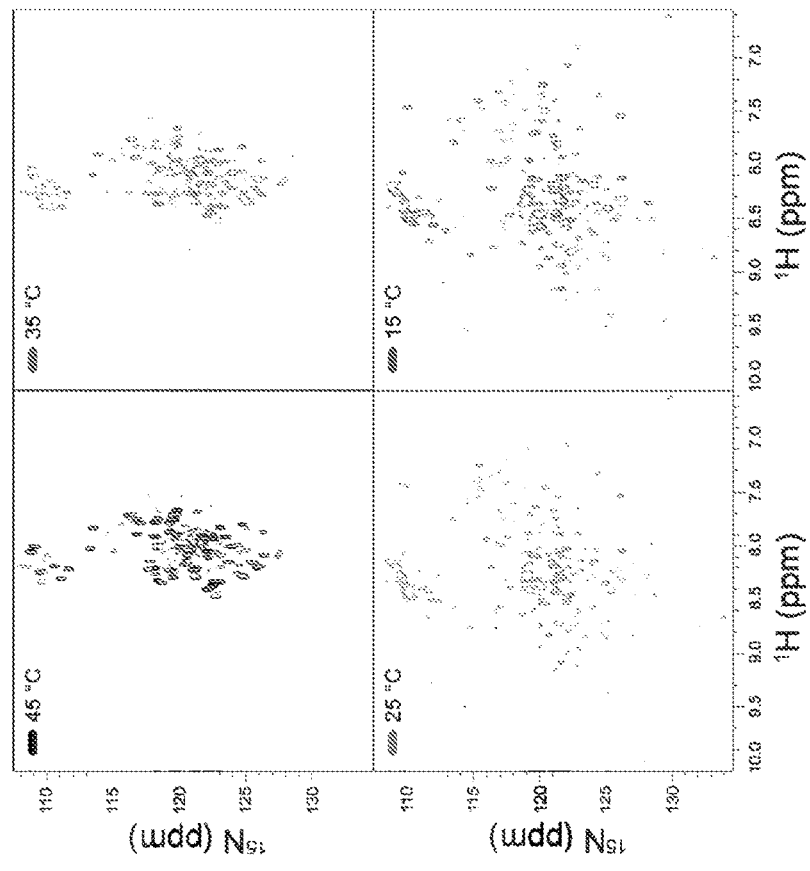
FIG. 8 illustrates four TROSY-HSQC NMR spectra collected during a temperature titration of TRPM8-VSD at four different temperatures.
Figure 9:
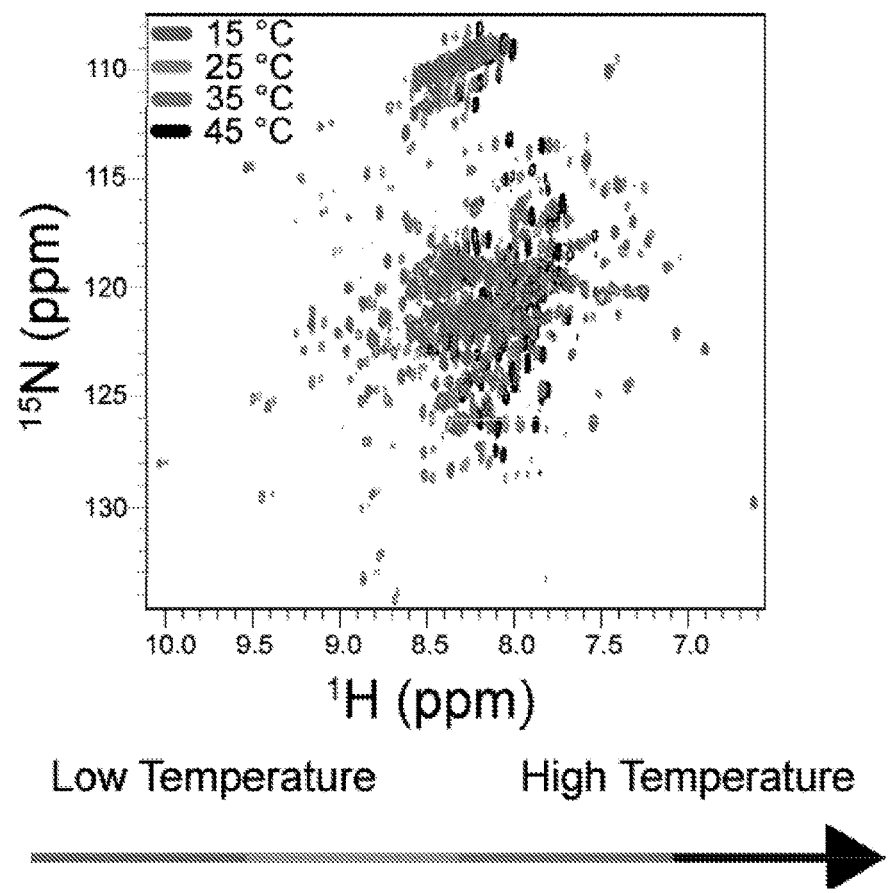
FIG. 9 illustrates one TROSY-HSQC NMR spectra representing the temperature titration of TRPM8-VSD at four different temperatures.
Figure 10:
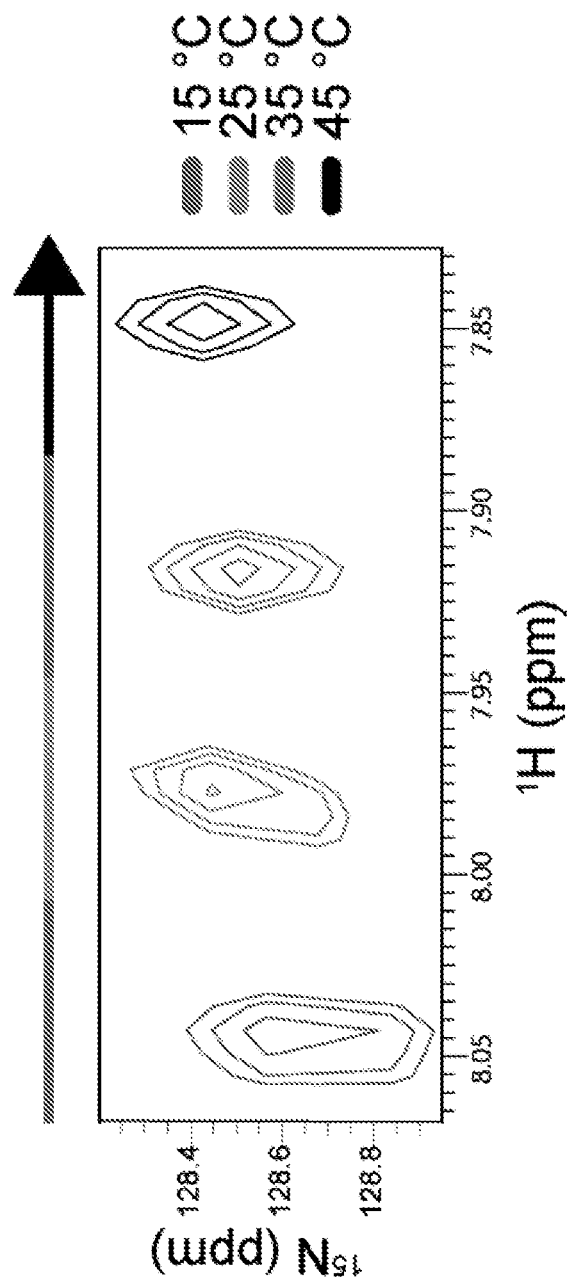
FIG. 10 illustrates a protein conformational shift of TRPM8-VSD represented by a shift in the TROSY-HSQC NMR spectra that correlates to temperature change.
Figure 11:
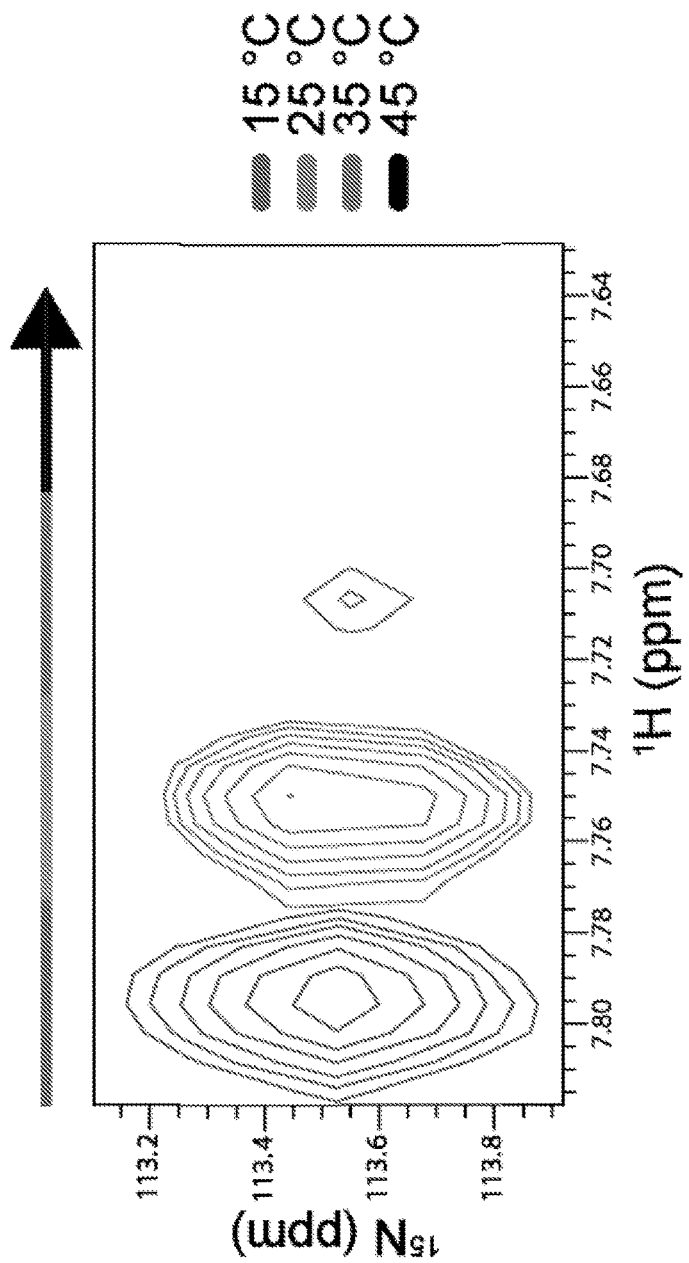
FIG. 11 illustrates a protein conformational shift of TRPM8-VSD represented by the absence of the TROSY-HSQC NMR spectra upon exposure of the protein domain to cold temperature.
Figure 12:
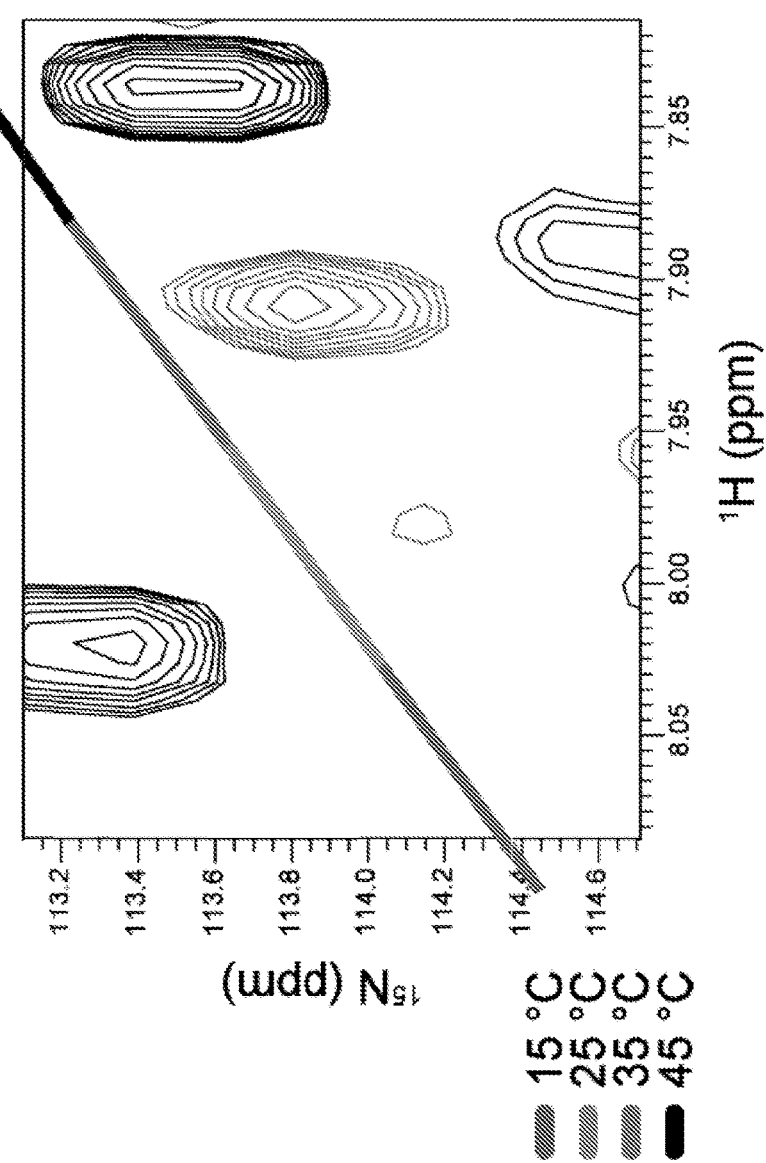
FIG. 12 illustrates a protein conformational shift of TRPM8-VSD represented by the presence of the TROSY-HSQC NMR spectra upon exposure of the protein domain to heated temperature.
Figure 13:
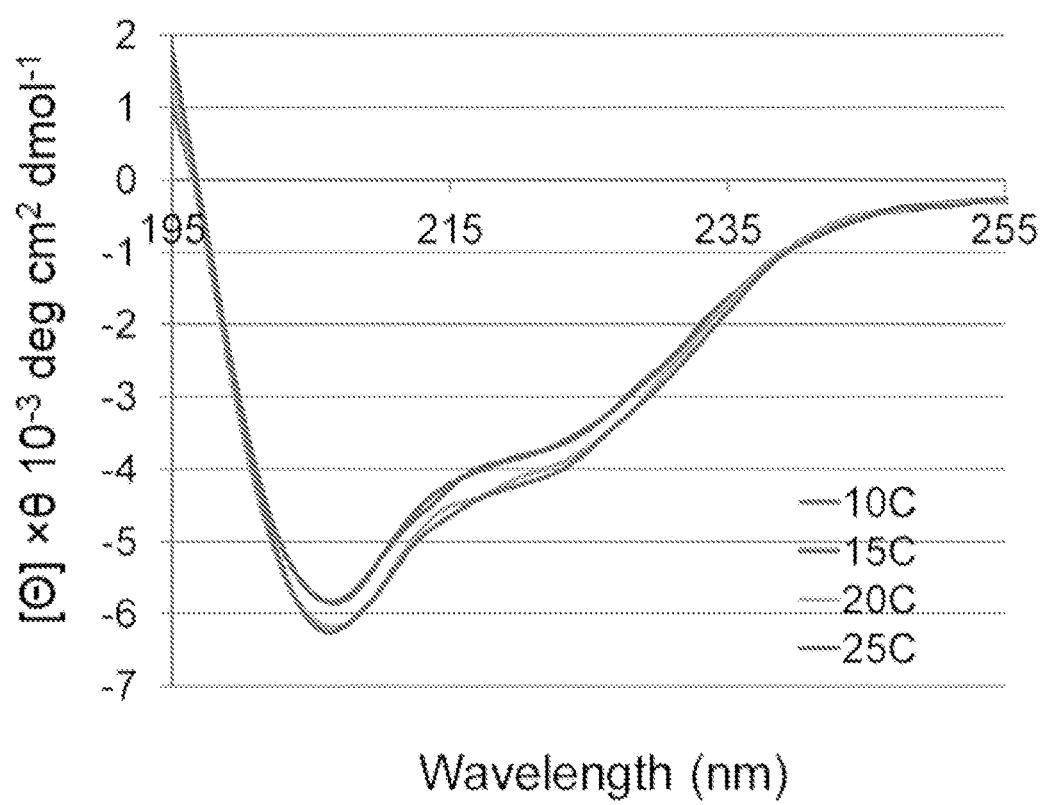
FIG. 13 is a circular dichroism (CD) spectra of the TRPM8-VSD during a temperature titration.
Figure 14:
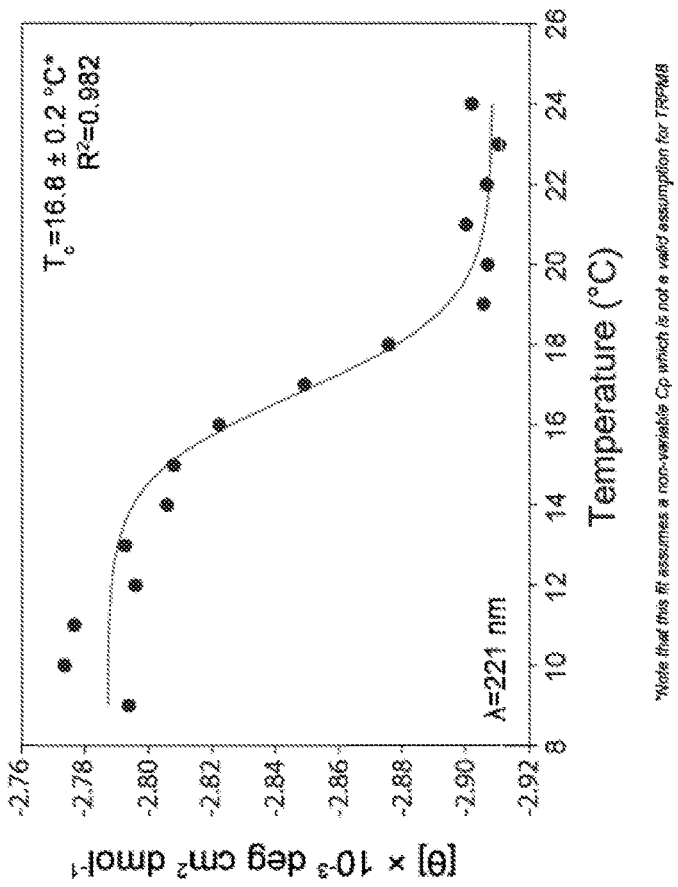
FIG. 14 is a plot of the CD spectra obtained from a temperature titration of TRPM8-VSD.

Similarly, the protein conformation modulation of TRPM8-VSD over a change in temperature (15° C., 25° C., 35° C., and 45° C.) can be observed in the TROSY-HSQC NMR spectra of FIGS. 8 and 9. Temperature perturbation is also observed by looking at the TROSY-HSQC NMR spectra of the temperature titration of TRPM8-VSD as shown in FIG. 10. Also in FIG. 10 the TROSY-HSQC NMR spectra are shown to shift from 8.05 ppm at a temperature of about 15° C. to about 7.85 ppm at a temperature of about 45° C. FIG. 11 illustrates the presence of TROSY-HSQC NMR spectra at 15° C. and 25° C. as well as the absence of spectra at 35° C. and 45° C.

WORKING EXAMPLE

We have engineered a gene fragment of a voltage-sensitive protein domain into a pET21b expression vector and transformed E. coli bacteria with this vector and then used the bacteria to express the voltage sensing domain. While the protein is expressed in a number of conditions, we have optimized expression which occurs at 18° C., once the cells reach an OD600 of about 0.7, they are induced with 0.3 mM IPTG for about 36 hours. The cells are then subjected to sonication for lysis. We then extract the membrane proteins with 0.3% empigen detergent, using about 100 mL of lysis buffer and centrifuge at 20K rpm for 20 mins to pellet the non-soluble fraction. The soluble fraction which contains the human TRPM8 VSD protein is then purified by both Ni-NTA affinity chromatography as well as gel filtration chromatography. We currently obtain about 2-3 mg of pure VSD per liter of bacterial culture.

During this process we can incorporate the VSD into many membrane mimics and evaluate the functional aspects of this domain. Under multiple detergent conditions we see significant conformational change as a function of temperature as measured by TROSY-HSQC NMR indicating that this is an intrinsic feature of this isolated TRPM8 domain. It is noteworthy that we identify structural perturbation in the regime where electrophsyiology has shown for the transition of the channel happens physiologically. In addition, biophysical techniques such as far UV CD isolate structural transitions that occur within about +/−2° C. of the physiological conformation change for the entire TRPM8 protein.

The use of this heterologously expressed protein could have significant use as a novel mechanism to regulate certain proteins or signaling cascades by simply associating or fusing this domain with other proteins or biomolecules. In addition, since there is significant development of TRPM8 as a therapeutic target, having the ability to isolate the VSD in known conformations could lead to more specific therapeutic development over what is traditionally done by screening the entire channel.

We describe a membrane protein domain that changes conformational structure as a function of temperature. We can generate milligrams of pure protein that could have impact or commercial potential in development of artificial ways to regulate biology, such as in synthetic biology by fusing this domain to other proteins which could in turn be turned on or off as a function of temperature. This domain is isolated from the TRPM8 protein which is a common target for therapeutic development. This protein domain, in addition to being used as a temperature switch, could form a basis of a platform for novel therapeutic screening against specific conformations of this temperature switch, which should increase both affinity and specificity to a given state of potential compounds.

Currently, there are polymorphic crystals that are available as molecular temperature switches but they are not compatible with biology nor could they be harnessed with the same precision to regulate molecular dynamics as a function of temperature. This invention is the first isolation of a protein-based temperature switch. With respect to drug screening, this offers a simplified platform that is conformational state specific which should allow for enhanced compounds.

For drug screening, it is clear that isomerization of compounds can effect efficacy and off target effects. Having the ability to fine tune the conformational state of the target should increase the efficacy of screening and development.

The materials and methods described above are not intended to be limited to the embodiments and examples described herein.

The invention claimed is:

1. A method of regulating protein conformation comprising:
   fusing a protein and a voltage sensing domain (VSD) of a TRPM8 protein (TRPM8-VSD) to form a protein chimera, wherein regulating a conformation of the protein chimera comprises changing a temperature such that the protein chimera conformation at a changed temperature varies from the protein chimera conformation at an initial temperature.

2. The method of claim 1 wherein the protein comprises a membrane protein domain.

3. The method of claim 1, further comprising detecting the varied protein chimera conformation at the changed temperature by TROSY-HSQC NMR.

4. The method of claim 1, wherein the changed temperature of the protein chimera comprises the initial temperature increased by about 2° C.

5. The method of claim 1, wherein the changed temperature of the protein chimera comprises the initial temperature decreased by about 2° C.

6. The method of claim 1, wherein the changed temperature comprises about 15° C.

7. The method of claim 1, wherein the changed temperature comprises about 25° C.

8. The method of claim 1, wherein the changed temperature comprises about 35° C.

9. The method of claim 1, wherein the changed temperature comprises about 45° C.

10. The method of claim 1, wherein regulating comprises contacting the TRPM8-VSD with menthol such that the protein chimera conformation after contact with the menthol differs from the protein chimera conformation prior to contact with the menthol.

11. A kit for protein conformation regulation comprising:
   A recombinantly expressed and isolated voltage sensing protein (VSD) domain of a TRPM8 protein (TRPM8-VSD), the TRPM8-VSD configured to regulate a protein conformation during a temperature change from an initial temperature to a changed temperature.

12. The kit of claim 11, wherein the changed temperature comprises about 2° C. higher than the initial temperature.

13. The kit of claim 11, wherein the changed temperature comprises about 2° C. lower than the initial temperature.

14. The kit of claim 11, wherein the changed temperature comprises about 15° C.

15. The kit of claim 11, wherein the changed temperature comprises about 45° C.

16. A method of making a recombinant protein including a temperature-induced conformation shift domain, comprising:
   recombinantly expressing a voltage sensing domain (VSD) of a TRPM8 protein (TRPM8-VSD); and
   fusing said TRPM8-VSD with another protein.

* * * * *

SEQUENCE LISTING

```
<160> NUMBER OF SEQ ID NOS: 3

<210> SEQ ID NO 1
<211> LENGTH: 336
<212> TYPE: PRT
<213> ORGANISM: Homo sapiens

<400> SEQUENCE: 1

Met Gly His His His His His Gly Leu Val Pro Arg Gly Ser Pro
1               5                   10                  15

Gly Val Gln Asn Phe Leu Ser Lys Gln Trp Tyr Gly Glu Ile Ser Arg
            20                  25                  30

Asp Thr Lys Asn Trp Lys Ile Ile Leu Cys Leu Phe Ile Ile Pro Leu
        35                  40                  45

Val Gly Cys Gly Phe Val Ser Phe Arg Lys Lys Pro Val Asp Lys His
    50                  55                  60

Lys Lys Leu Leu Trp Tyr Tyr Val Ala Phe Phe Thr Ser Pro Phe Val
65                  70                  75                  80

Val Phe Ser Trp Asn Val Val Phe Tyr Ile Ala Phe Leu Leu Leu Phe
                85                  90                  95

Ala Tyr Val Leu Leu Met Asp Phe His Ser Val Pro His Pro Pro Glu
            100                 105                 110
```

```
Leu Val Leu Tyr Ser Leu Val Phe Val Leu Phe Cys Asp Glu
            115                 120                 125

Val Arg Gln Trp Tyr Val Asn Gly Val Asn Tyr Phe Thr Asp Leu Trp
130                 135                 140

Asn Val Met Asp Thr Leu Gly Leu Phe Tyr Phe Ile Ala Gly Ile Val
145                 150                 155                 160

Phe Arg Leu His Ser Ser Asn Lys Ser Ser Leu Tyr Ser Gly Arg Val
            165                 170                 175

Ile Phe Cys Leu Asp Tyr Ile Ile Phe Thr Leu Arg Leu Ile His Ile
            180                 185                 190

Phe Thr Val Ser Arg Asn Leu Gly Pro Lys Ile Ile Met Leu Gln Arg
            195                 200                 205

Met Leu Ile Asp Val Phe Phe Phe Leu Phe Leu Phe Ala Val Trp Met
            210                 215                 220

Val Ala Phe Gly Val Ala Arg Gln Gly Ile Leu Arg Gln Asn Glu Gln
225                 230                 235                 240

Arg Trp Arg Trp Ile Phe Arg Ser Val Ile Tyr Glu Pro Tyr Leu Ala
                    245                 250                 255

Met Phe Gly Gln Val Pro Ser Asp Val Asp Gly Thr Thr Tyr Asp Phe
            260                 265                 270

Ala His Cys Thr Phe Thr Gly Asn Glu Ser Lys Pro Leu Cys Val Glu
            275                 280                 285

Leu Asp Glu His Asn Leu Pro Arg Phe Pro Glu Trp Ile Thr Ile Pro
            290                 295                 300

Leu Val Cys Ile Tyr Met Leu Ser Thr Asn Ile Leu Leu Val Asn Leu
305                 310                 315                 320

Leu Val Ala Met Phe Gly Tyr Thr Val Gly Thr Val Gln Glu Asn Asn
            325                 330                 335

<210> SEQ ID NO 2
<211> LENGTH: 301
<212> TYPE: PRT
<213> ORGANISM: Homo sapiens

<400> SEQUENCE: 2

Asn Trp Lys Ile Ile Leu Cys Leu Phe Ile Ile Pro Leu Val Gly Cys
1               5                   10                  15

Gly Phe Val Ser Phe Arg Lys Lys Pro Val Asp Lys His Lys Lys Leu
            20                  25                  30

Leu Trp Tyr Tyr Val Ala Phe Phe Thr Ser Pro Phe Val Val Phe Ser
            35                  40                  45

Trp Asn Val Val Phe Tyr Ile Ala Phe Leu Leu Leu Phe Ala Tyr Val
50                  55                  60

Leu Leu Met Asp Phe His Ser Val Pro His Pro Pro Glu Leu Val Leu
65                  70                  75                  80

Tyr Ser Leu Val Phe Val Leu Phe Leu Phe Cys Asp Glu Val Arg Gln
                85                  90                  95

Trp Tyr Val Asn Gly Val Asn Tyr Phe Thr Asp Leu Trp Asn Val Met
            100                 105                 110

Asp Thr Leu Gly Leu Phe Tyr Phe Ile Ala Gly Ile Val Phe Arg Leu
            115                 120                 125

His Ser Ser Asn Lys Ser Ser Leu Tyr Ser Gly Arg Val Ile Phe Cys
            130                 135                 140

Leu Asp Tyr Ile Ile Phe Thr Leu Arg Leu Ile His Ile Phe Thr Val
```

```
                145             150             155             160
        Ser Arg Asn Leu Gly Pro Lys Ile Ile Met Leu Gln Arg Met Leu Ile
                        165             170             175

Asp Val Phe Phe Phe Leu Phe Leu Phe Ala Val Trp Met Val Ala Phe
                        180             185             190

Gly Val Ala Arg Gln Gly Ile Leu Arg Gln Asn Glu Gln Arg Trp Arg
                        195             200             205

Trp Ile Phe Arg Ser Val Ile Tyr Glu Pro Tyr Leu Ala Met Phe Gly
                        210             215             220

Gln Val Pro Ser Asp Val Asp Gly Thr Thr Tyr Asp Phe Ala His Cys
        225             230             235             240

Thr Phe Thr Gly Asn Glu Ser Lys Pro Leu Cys Val Glu Leu Asp Glu
                        245             250             255

His Asn Leu Pro Arg Phe Pro Glu Trp Ile Thr Ile Pro Leu Val Cys
                        260             265             270

Ile Tyr Met Leu Ser Thr Asn Ile Leu Leu Val Asn Leu Leu Val Ala
                        275             280             285

Met Phe Gly Tyr Thr Val Gly Thr Val Gln Glu Asn Asn
                        290             295             300

<210> SEQ ID NO 3
<211> LENGTH: 137
<212> TYPE: PRT
<213> ORGANISM: Homo sapiens

<400> SEQUENCE: 3

Met Thr Met Glu Thr Leu Pro Lys Val Leu Glu Val Asp Glu Lys Ser
1               5                   10                  15

Pro Glu Ala Lys Asp Leu Leu Pro Ser Gln Thr Ala Ser Ser Leu Cys
                20                  25                  30

Ile Ser Ser Arg Ser Glu Ser Val Trp Thr Thr Thr Pro Arg Ser Asn
                35                  40                  45

Trp Glu Ile Tyr Arg Lys Pro Ile Val Ile Met Ser Val Gly Gly Ala
        50                  55                  60

Ile Leu Leu Phe Gly Val Val Ile Thr Cys Leu Ala Tyr Thr Leu Lys
65                  70                  75                  80

Leu Ser Asp Lys Ser Leu Ser Ile Leu Lys Met Val Gly Pro Gly Phe
                85                  90                  95

Leu Ser Leu Gly Leu Met Met Leu Val Cys Gly Leu Val Trp Val Pro
                100                 105                 110

Ile Ile Lys Lys Lys Gln Lys His Arg Gln Lys Ser Asn Phe Leu Arg
                115                 120                 125

Ser Leu Lys Ser Phe Phe Leu Thr Arg
                130             135
```